(12) United States Patent
Mausbach et al.

(10) Patent No.: US 6,540,967 B2
(45) Date of Patent: Apr. 1, 2003

(54) APPARATUS FOR THE IRRADIATION OF A LIQUID

(75) Inventors: Klaus Mausbach, Neuried (DE); Johann Heith, Vienna (DE)

(73) Assignee: Pathogenex GmbH, Martinsried (DE)

( * ) Notice: Subject to any disclaimer, the term of this patent is extended or adjusted under 35 U.S.C. 154(b) by 146 days.

(21) Appl. No.: 09/759,607

(22) Filed: Jan. 12, 2001

(65) Prior Publication Data

US 2002/0008210 A1 Jan. 24, 2002

(30) Foreign Application Priority Data

Jul. 15, 1998 (DE) .......................... 198 31 768

(51) Int. Cl.⁷ ............................... B01J 19/08
(52) U.S. Cl. ...................... 422/186.3; 422/24
(58) Field of Search ................. 422/186.3, 24

(56) References Cited

U.S. PATENT DOCUMENTS

| 4,748,120 A | 5/1988 | Wiesehahn |
| 5,133,932 A | 7/1992 | Gunn et al. |
| 5,567,616 A | 10/1996 | Dill, II |

FOREIGN PATENT DOCUMENTS

| DE | 42 28 535 | 3/1994 |
| DE | 44 06 759 | 9/1995 |
| DE | 44 40 880 | 5/1996 |
| EP | 0 240 154 | 10/1987 |
| GB | 655198 | 7/1951 |

OTHER PUBLICATIONS

Habel et al., "A Continuous Flow Method of Exposing Antigens to Ultraviolet Radiation," 1947, pp. 273–279.
International Search Report for application No. PCT/EP99/05055, mailed Nov. 9, 1999.
International Preliminary Examination Report for application No. PCT/EP99/05055, mailed Nov. 8, 2000.

*Primary Examiner*—K. Mayekar
(74) *Attorney, Agent, or Firm*—Meyertons Hood Kivlin Kowert & Goetzel, P.C.; Jeffrey C. Hood

(57) ABSTRACT

The invention relates to an apparatus for the irradiation, in particular UV irradiation, of a liquid. The irradiation takes place in this case under precisely defined and reproducible operating conditions. The apparatus has a rotating cylinder with an upper inflow, a lower outflow and an irradiation unit, the cylinder forming an angle of inclination ($\alpha$) with the horizontal. The lower outflow also has two connections for passing on the liquid, one connection being closable with the aid of a first control unit if the irradiation of the liquid deviates from the defined conditions.

22 Claims, 2 Drawing Sheets

APPARATUS FOR THE IRRADIATION OF A LIQUID

FIELD OF THE INVENTION

The invention relates to an apparatus for the irradiation, in particular the UV irradiation, of a liquid. The irradiation in this case takes place under precisely defined conditions. The apparatus according to the invention is therefore suitable in particular for the inactivation of viruses and other pathogens in biological liquids, in particular in blood serums.

It is known to irradiate biological liquids with intensive ultraviolet light for the inactivation of viruses and other pathogens. Other methods are, for example, gamma irradiation and microwave treatment. The rate of absorption of serums and other biological liquids is several orders of magnitude greater than that of normal water, which is often likewise irradiated with UV light for removing bacteria. On account of the high rate of absorption, the serums are irradiated in the form of a thin layer, in order to ensure full inactivation. The layer thickness of the serums during the UV irradiation is generally of an order of magnitude below 0.5 mm. Furthermore, the spectrum of the UV light radiated in is modulated in such a way that protein damage is avoided.

A device for carrying out the described treatment of serums was described back in 1947 (Habel, Sockrider, Journal of Immunology 56 (1947) 273–279). This concerns a rotating cylinder inclined slightly with respect to the horizontal. The liquid to be irradiated is applied to the inner side of the rotating cylinder. It is then pressed by the centrifugal force against the inside wall in the form of the required thin layer. On account of the inclination of the cylinder, the liquid is slowly passed through the cylinder and leaves it after approximately 8 seconds. One or more UV lamps are fixedly arranged along the axes of the rotating cylinder.

In another type of device, in the end individual parts by volume of the liquid in the form of a thin layer are exposed to the UV light, cf. U.S. Pat. No. 5,133,932. In this case it cannot be ensure at the irradiation will cover all parts by volume and consequently completely kill off the viruses in the liquid.

In the case of another type of device, the liquid is passed through thin capillaries coiled around the UV lamp, cf. U.S. Pat. No. 4,748,120. Capillary diameters of less than 1 mm are used in this case. However, only a low throughput is achieved as a result.

Taking these points into consideration, today devices of the first-mentioned category are frequently used for the inactivation of viruses and other pathogens in biological liquids, i.e. devices which are based on the publication by Habel et al. from 1947. U.S. Pat. No. 5,567,616 likewise discloses an apparatus which essentially corresponds in its construction to the principle of the device described back in 1947.

However, when this type of device, with a rotating inclined cylinder, has been used, it has repeatedly been the case that not all the viruses are killed off, on account of defective operating conditions. In these cases, considerable amounts of possibly defectively treated blood preparations had to be subsequently withdrawn, without however establishing sufficient certainty as to the cause and extent of the defective irradiation.

It is therefore the object of the present invention to provide an apparatus for the irradiation of liquids, in particular biological liquids, such as serums, which has safety devices for the avoidance or early detection of improper irradiation.

SUMMARY OF THE INVENTION

This object is achieved by the apparatus according to the invention. This apparatus for the irradiation of a liquid under defined conditions has a rotating cylinder with an upper inflow, a lower outflow and an irradiation unit, the cylinder forming an angle of inclination ($\alpha$) with the horizontal. The inclined cylinder rotates about its own axis. The liquid to be irradiated is introduced into the upper inflow. The introduced liquid is pressed by the centrifugal force against the inside wall of the cylinder, where it forms the required thin layer. A plurality of UV lamps for the irradiation of the liquid layer are fitted along the axis of the cylinder, ensuring intensive irradiation of the liquid. For the inactivation of the viruses and pathogens in biological liquids, such as in blood serums for example, light, in particular UVC light, is used. Light at a wavelength of 254 nm is preferably used for this. Irradiation at this wavelength leads on the one hand to relatively low protein damage and also, however, on the other hand to effective virus inactivation. In addition, mercury lamps which radiate the same wavelength can also be used for this purpose. Furthermore, laser light can also be used.

According to the invention, the lower outflow has two connections for passing on the liquid, one connection being closable with the aid of a first control unit if the irradiation of the liquid deviates from the defined conditions. In this case, the liquid can only pass the second connection, i.e. the unclosable connection. Consequently, once the first connection has been closed, that is after a problem has arisen with the irradiation, the liquid can be diverted into another container, that is to say be collected separately from the amount of liquid already irradiated under normal conditions. Correctly and possibly incorrectly irradiated amounts of liquid are consequently separated, so that any contamination of reliably irradiated serum with viruses is ruled out.

In a preferred embodiment, a second control unit is provided; which switches off the irradiation unit and/or interrupts the upper inflow if the irradiation deviates from the defined conditions.

Furthermore, in a further preferred embodiment, the apparatus according to the invention has a monitoring and documentation unit for at least one, preferably all, of the following parameters:
 a) intensity of the irradiation,
 b) rotational speed of the cylinder,
 c) angle of inclination ($\alpha$) of the cylinder,
 d) temperature of the liquid before and after the irradiation,
 e) layer thickness of the liquid within the cylinder,
 f) flow rate of the liquid through the cylinder.

These parameters are measured and documented at time intervals which can be freely set, whereby a chronologically complete documentation of the operating state is obtained. These operating data are preferably logged twice, to be specific both on a printer and on a storage medium, for example an exchangeable hard disk or a zip drive, which can be sealed and the tape of which can be exchanged at fixed intervals. The storage medium is required to ensure parameter storage in the event of failure of the printer. Furthermore, the recording on the storage medium may serve as forgery proof evidence of the operating conditions which is accessible only to selected persons, for instance the device manufacturer. Furthermore, the permanent storage on a data medium may also serve the purpose of providing the user with a statistical overview of his parameters. This achieves the effect that the respective operating conditions can be reconstructed later at any time and for a particular batch.

The monitoring and documentation unit according to the invention is preferably coupled to the first control unit and, if there is one, also to the second control unit in such a way that, if one or more of the parameters falls below a given minimum value or exceeds a given maximum value, the first control unit closes the closable connection of the lower outflow and the second control unit switches off the irradiation unit. If, for example, the lamps are too weak or fail entirely, the irradiation is automatically interrupted. At the same time, the inflow of the liquid into the rotating cylinder is ended. Furthermore, the closable connection at the lower outflow is closed by the first control unit, so that the remaining liquid located in the cylinder at this point in time is diverted through the second connection at the lower outflow into a separate container. Contamination of the already irradiated amount of liquid is avoided as a result. The second connection is preferably arranged at the lower outflow in such a way that the liquid flowing out from the cylinder passes the second connection only if the first closable connection is closed. In practice, this can be achieved for example by the second connection being directed upwards with an adequately great inclination, while the first, closable connection has at least a smaller inclination upwards, but preferably points downwards, so that when the first connection is not closed the liquid always flows through it for gravitational reasons.

The intensity of the irradiation may be registered for example by measuring the lamp current and concluding the intensity then delivered. Another possible way is to arrange measuring sensors in the vicinity of the lamps, it being possible for the intensity to be measured directly, so that conclusions, with the associated uncertainties, are not necessary.

The rotational speed and the angle of inclination of the cylinder can be measured in a conventional way with suitable mechanical or electronic sensors.

As already mentioned, the temperature of the liquid before and after the irradiation is also measured and monitored by corresponding sensors, provided in the monitoring and documentation unit. The optimum temperature of the liquid to be irradiated during the irradiation lies in a range between 4° C. and 8° C. If the temperature becomes too high, this can lead to permanent damage to the proteins, if it becomes too low, the viscosity of the liquid changes, so that the formation of a homogeneous liquid layer is made more difficult. Consequently, in a preferred embodiment of the apparatus according to the invention, if the temperature at the temperature sensors, preferably arranged at the inflow and outflow, deviates from the optimum temperature values, the output of the cooling means is changed in such a way as to attempt to regain the optimum temperature. If this is not possible, the irradiation is ended and the liquid located in the cylinder at this point in time is diverted via the second connection of the lower outflow into a separate container by means of the already mentioned coupling according to the invention between the monitoring and documentation unit and the first and second control units. The upper limit temperature lies at approximately 25° C., the lower limit temperature lies at approximately 0° C.

Furthermore, the thickness of the liquid layer is also continually measured and monitored by means of the monitoring and documentation unit according to the invention. The thickness of the liquid layer should normally be of the order of magnitude of below 0.5 mm. In a preferred embodiment, the layer thickness is measured with the aid of an interferometer. The interferometer comprises a transmitter module, which can for example be installed at the upper end of the rotating cylinder, and a receiver module, which can for example be attached to the lower end of the said cylinder. The transmitter generally comprises a laser, the light beam of which impinges obliquely on the surface of the irradiated liquid. Part of this light beam is reflected directly at the surface of the liquid, the rest penetrates into the liquid and is reflected at the liquid/cylinder inside wall interface. The two reflected partial beams impinge on the sensor. The shift of the second light beam in relation to the first is proportional to the thickness of the liquid layer. The laser/sensor system operates in a wavelength range which is not influenced by the UVC irradiation preferably used, to prevent any disturbance of the layer thickness measurement. This type of layer thickness measurement consequently also has the advantage of being independent of all the other parameters of the apparatus. Previously, the layer thickness was usually determined by intensity measurements of the light used for the irradiation of the liquid layer after transmission through the liquid layer. This had the consequence on the one hand that the corresponding sensor had to be arranged behind the liquid layer, and consequently outside the cylinder, which was not very practical for the handling of the apparatus, and on the other hand that the layer thickness measurement was also subject to the influence of other parameters, not only that of the actual layer thickness. Transmission measurements can, for example, be falsified by thicknesses or density variations of the cylinder wall, as well as by a usually unavoidable drift of the lamps occurring over time. In addition, in the case of such a transmission measurement it is necessary whenever the liquid to be irradiated is changed for a new calibration to this specific liquid to be carried out. By contrast, in the case of interferometry, only the easily determinable refractive index of the liquid respectively to be irradiated is required. As an alternative to fixed mounting of the interferometer within the cylinder, the interferometer may also be mounted movably within the cylinder, for example in a rotating and upwardly and downwardly movable manner on the inner axis of the cylinder. This makes it possible to determine the layer thickness of the liquid layer at any point of the cylinder inside wall.

In a further preferred embodiment of the apparatus according to the invention, as an alternative to the interferometric method, the layer thickness is determined capacitively. This can be realized, for example, by the arrangement of a cylindrical wire netting around the cylinder axis of the apparatus at a defined distance from the inside wall of the cylinder. The wire netting and the rotating cylinder represent a capacitor, the capacitance of which is determined inter alia by the medium between its two capacitor plates. This medium in this case comprises parts of the gas atmosphere, which is present inside the cylinder, and of the liquid layer, the dielectric property of which consequently plays a part in determining the capacitance of the capacitor. If the layer thickness of the liquid changes, the capacitance of the capacitor consequently also changes; the capacitance of this capacitor can be measured at any time by an oscillating circuit.

In a further preferred embodiment of the apparatus according to the invention, the apparatus has a motor for adjusting the angle of inclination ($\alpha$) of the cylinder. This motor is preferably coupled to the monitoring and documentation unit according to the invention. If the intensity of the UVC irradiation of the lamps decreases as a consequence of the natural ageing process of the lamps, the inclination of the cylinder is also changed according to the invention with the aid of the motor in the direction of a flatter setting. The residence time of the liquid to be irradiated in the cylinder is prolonged as a result. If the angle of inclination falls below a previously set minimum value, which generally lies at approximately 2°, a fault message is triggered and the irradiation is ended with the aid of the second control unit.

If the thickness of the liquid layer changes spontaneously or under the influence of the control loop just described, comprising the UV sensor and the angle-of-inclination motor, the output of the pump, i.e. the pumping rate, is preferably adapted. If the layer thickness still becomes too great in spite of a reduced pumping output, the irradiation is in turn ended by means of the second control unit and/or the upper inflow is interrupted.

In another preferred embodiment of the invention, it is likewise ensured by means of a coupling of the pump to the monitoring and documentation unit that, if the flow rate of the liquid deviates from a given value, the output of the pump is changed in such a way that the given value for the flow rate is reached again. If this is not possible, the irradiation unit is switched off and/or the upper inflow for the liquid is interrupted.

In a further preferred embodiment of the invention, an alarm unit is provided, which always triggers an alarm if one or more of the parameters mentioned above, to be specific for the intensity of the irradiation, for the rotational speed of the cylinder, for the angle of inclination ($\alpha$) of the cylinder, for the temperature of the liquid before and after the irradiation and for the layer thickness of the liquid within the cylinder, falls below or exceeds a given minimum or maximum value. As a result, in the event of a problem occurring, the user of the apparatus according to the invention immediately receives notification of the problem independently of the automatic switching off of the irradiation by the second control unit and the automatic diversion of the defectively irradiated liquid which was located within the cylinder at the point in time of the problem through the unclosable connection at the lower outlet into a separate container.

BRIEF DESCRIPTION OF THE DRAWINGS

Further advantages, features and application possibilities of the invention emerge from the following description of an exemplary embodiment in conjunction with the drawing, in which.

DETAILED DESCRIPTION OF THE INVENTION

Figure 1:
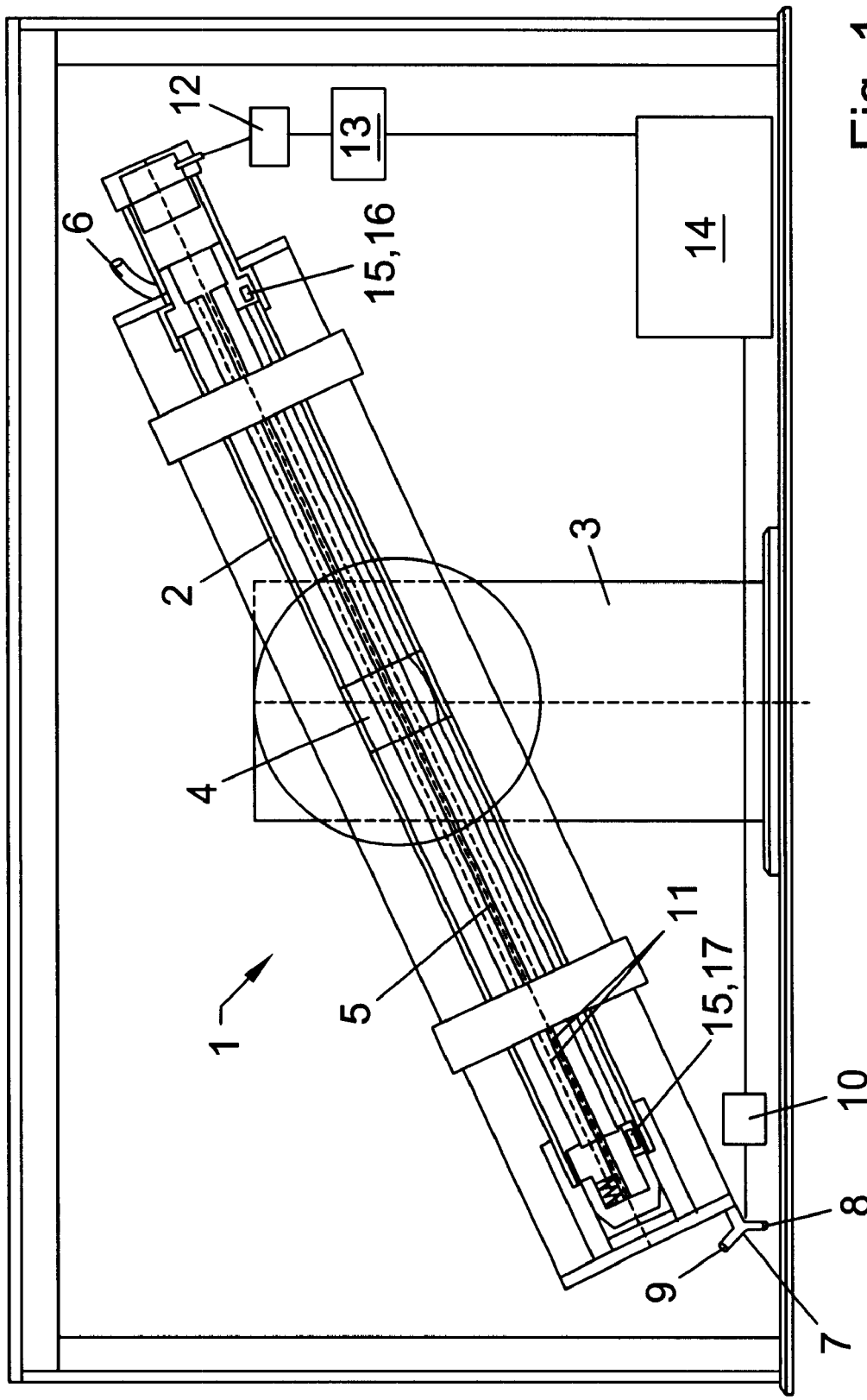
FIG. 1 shows a side view of an apparatus according to the invention for the irradiation of a liquid.

In FIG. 1, a side view of an apparatus 1 according to the invention is represented. The apparatus 1 according to the invention shown here comprises a cylinder 2, which is mounted rotatably on a supporting device 3. The angle of inclination $\alpha$, which the cylinder 2 forms with the horizontal, can be set as desired within wide limits by means of a motor 4. The angle of inclination is preferably approximately 10°. The cylinder 2 can be set in rotation about the cylinder axis 5 by a further motor. The rotational speed of the cylinder 2 can be varied according to the variable output of the motor. As a rule, the speed is approximately 150 revolutions per minute. The liquid to be irradiated is introduced through the upper inflow 6 in the cylinder 2. The introduced liquid is pressed by the centrifugal force brought about by the rotation of the cylinder 2 against the inside wall of the cylinder 2, where it forms the required thin layer. Depending on the inclination of the cylinder 2, the liquid flows at a corresponding speed along the inside wall of the cylinder 2 as far as the outflow 7. The outflow 7 has two connections 8 and 9, connection 8 being closable, for example by a valve. A first control unit 10 is provided, with the aid of which connection 8 can be closed. A plurality of UV lamps 1, with the aid of which the liquid layer is irradiated, are fixedly mounted along the cylinder axis 5. The UV lamps 11 are supplied by a separate supply 12. For inactivating the viruses and/or other pathogens, light at a wavelength in the range around 254 nm is preferably used. With the aid of a second control unit 13, the irradiation can be discontinued, that is to say it allows the UV lamps 11 to be switched off. Both control units 10 and 13 are coupled to a monitoring and documentation unit 14 according to the invention. The monitoring and documentation unit 14 has sensors of various types, with the aid of which the various parameters essential for the effective irradiation of the liquid can be measured. The intensity of the irradiation, that is to say the intensity of the UV lamps 11, is determined for example by means of a measurement of the lamp current; the corresponding signal is consequently supplied by an ammeter. UVC sensors can also be used here. The rotational speed and the angle of inclination of the cylinder 2 are determined by means of electronic or mechanical sensors, the temperature is determined with suitable thermocouples or temperature sensors and the layer thickness is determined with an interferometer 15. The interferometer 15 comprises a transmitter module 16, to be specific a laser which is installed at the upper end of the cylinder 2, and a receiver module 17, which can be attached to the lower end of the cylinder 2. The monitoring and documentation unit 14 also has a printer and a further sealable storage medium, to allow the operating data to be logged and reproduced.

Figure 2:
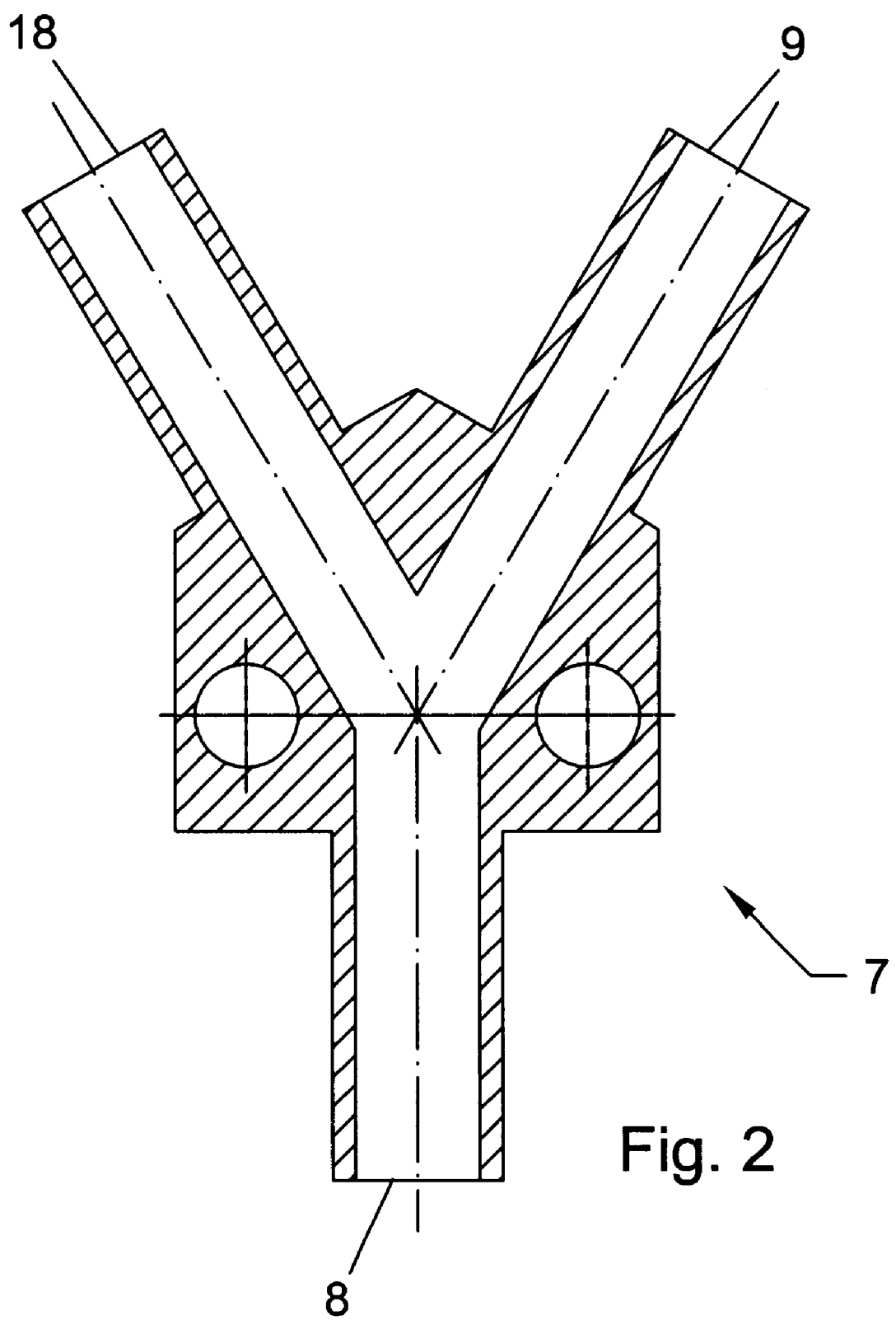
FIG. 2 shows an enlarged view of the outflow according to the invention of the cylinder of another apparatus according to the invention for the irradiation of a liquid.

FIG. 2 shows a configuration according to the invention of the lower outflow 7 on the cylinder 2. Apart from the inlet 18 from the interior space of the cylinder 2, the two connections 8 and 9 of the outflow 7 of the cylinder 2 can be seen, connection 8 being closable, for example by means of a valve. In the preferable embodiment represented here, the geometrical arrangement of the connections 8 and 9 is such that connection 8 points vertically downwards, while the unclosable connection 9 points obliquely upwards. This achieves the effect that, when connection 8 is open, the irradiated liquid always flows away through this connection for gravitational reasons, and seeks the path through connection 9 only when connection 8 is closed.

We claim:

1. Apparatus for the irradiation of a liquid under defined conditions having a rotating cylinder with an upper inflow, a lower outflow and an irradiation unit, the cylinder forming an angle of inclination ($\alpha$) with the horizontal, wherein the lower outflow has two connections for passing on the liquid, one connection being closable with the aid of a first control unit if the irradiation of the liquid deviates from the defined conditions.

2. Apparatus according to claim 1, further comprising a second control unit, which switches off the irradiation unit and/or interrupts the upper inflow if the irradiation deviates from the defined conditions.

3. Apparatus according to claim 1, further comprising a monitoring and documentation unit for monitoring and recording at least one of the following parameters:
   a) intensity of the irradiation,
   b) rotational speed of the cylinder,
   c) angle of inclination ($\alpha$) of the cylinder,
   d) temperature of the liquid before and after the irradiation,
   e) layer thickness of the liquid within the cylinder,
   f) flow rate of the liquid through the cylinder.

4. Apparatus according to claim 3, further comprising a second control unit which switches off the irradiation unit and/or interrupts the upper inflow if the irradiation deviates from the defined conditions;
   wherein the monitoring and documentation unit is coupled to the first control unit and to the second control unit in such a way that, if one or more of the parameters a) to e) falls below a given minimum value or exceeds a given maximum value, the first control unit closes the closable connection of the lower outflow and the second control unit switches off the irradiation unit and/or interrupts the upper inflow.

5. Apparatus according to claim 3, further comprising an alarm unit which triggers an alarm if one or more of the parameters a) to e) falls below or exceeds a given minimum or maximum value.

6. Apparatus according to claim 1, further comprising an interferometer for measuring the layer thickness of the liquid within the cylinder.

7. Apparatus according to one of claim 1, further comprising a capacitive measuring device for determining the layer thickness of the liquid within the cylinder.

8. Apparatus according to claim 1, further comprising a motor for adjusting the angle of inclination ($\alpha$) of the cylinder.

9. Apparatus according to claim 8, wherein the motor for adjusting the angle of inclination ($\alpha$) of the cylinder is coupled to the monitoring and documentation unit in such a way that the angle of inclination ($\alpha$) of the cylinder is adapted according to the intensity of the irradiation.

10. Apparatus according to claim 1, further comprising a pump for introducing the liquid into the upper inflow of the cylinder which is coupled to the monitoring and documentation unit in such a way that the output of the pump is adapted according to the layer thickness of the liquid.

11. Apparatus according to claim 10, wherein the pump is coupled to the monitoring and documentation unit in such a way that, if the flow rate of the liquid deviates from a given value, the output of the pump is changed in such a way that the given value for the flow rate is reached again.

12. Apparatus for the irradiation of a liquid under defined conditions, comprising:
   a rotating cylinder, comprising:
      an upper inflow;
      a lower outflow; and
      an irradiation unit;
   wherein the cylinder forms an angle of inclination ($\alpha$) with the horizontal, and a first control unit, wherein the lower outflow has two connections for passing on the liquid, wherein the first control unit is operable to close one connection if the irradiation of the liquid deviates from the defined conditions.

13. Apparatus according to claim 12, further comprising:
   a second control unit, which switches off the irradiation unit and/or interrupts the upper inflow if the irradiation deviates from the defined conditions.

14. Apparatus according to claim 12, wherein the apparatus further comprises: a monitoring and documentation unit for monitoring and recording at least one of the following parameters:
   a) intensity of the irradiation,
   b) rotational speed of the cylinder,
   c) angle of inclination ($\alpha$) of the cylinder,
   d) temperature of the liquid before and after the irradiation,
   e) layer thickness of the liquid within the cylinder,
   f) flow rate of the liquid through the cylinder.

15. Apparatus according to claim 14, wherein the monitoring and documentation unit is coupled to the first control unit and to the second control unit in such a way that, if one or more of the parameters a) to e) falls below a given minimum value or exceeds a given maximum value, the first control unit closes the closable connection of the lower outflow and the second control unit switches off the irradiation unit and/or interrupts the upper inflow.

16. Apparatus according to claim 14, wherein the apparatus further comprises: an alarm unit which triggers an alarm if one or more of the parameters a) to e) falls below or exceeds a given minimum or maximum value.

17. Apparatus according to claim 12, further comprising:
   an interferometer for measuring the layer thickness of the liquid within the cylinder.

18. Apparatus according to one of claims 12, further comprising: a capacitive measuring device for determining the layer thickness of the liquid within the cylinder.

19. Apparatus according to claim 12, further comprising:
   a motor for adjusting the angle of inclination ($\alpha$) of the cylinder.

20. Apparatus according to claim 19,
   wherein the motor for adjusting the angle of inclination ($\alpha$) of the cylinder is coupled to the monitoring and documentation unit in such a way that the angle of inclination ($\alpha$) of the cylinder is adapted according to the intensity of the irradiation.

21. Apparatus according to claim 12, further comprising:
   a pump for introducing the liquid into the upper inflow of the cylinder which is coupled to the monitoring and documentation unit in such a way that the output of the pump is adapted according to the layer thickness of the liquid.

22. Apparatus according to claim 21,
   wherein the pump is coupled to the monitoring and documentation unit in such a way that, if the flow rate of the liquid deviates from a given value, the output of the pump is changed in such a way that the given value for the flow rate is reached again.

* * * * *